US009526487B2

(12) United States Patent
Rahmani

(10) Patent No.: US 9,526,487 B2
(45) Date of Patent: Dec. 27, 2016

(54) METHODS AND APPARATUSES FOR DELIVERING ANCHORING DEVICES INTO BODY PASSAGE WALLS

(75) Inventor: Emad Y. Rahmani, Indianapolis, IN (US)

(73) Assignee: Indiana University Research & Technology Corporation, Indianapolis, IN (US)

( * ) Notice: Subject to any disclaimer, the term of this patent is extended or adjusted under 35 U.S.C. 154(b) by 635 days.

(21) Appl. No.: 12/328,523

(22) Filed: Dec. 4, 2008

(65) Prior Publication Data
US 2009/0204147 A1    Aug. 13, 2009

Related U.S. Application Data

(60) Provisional application No. 60/992,508, filed on Dec. 5, 2007.

(51) Int. Cl.
*A61B 17/04* (2006.01)
*A61B 17/00* (2006.01)

(52) U.S. Cl.
CPC .. *A61B 17/0401* (2013.01); *A61B 2017/00296* (2013.01); *A61B 2017/0409* (2013.01); *A61B 2017/0417* (2013.01)

(58) Field of Classification Search
CPC ............ A61B 17/0401; A61B 1/00089; A61B 2017/00296; A61B 2017/0409; A61B 2017/0417; A61F 5/0069; A61F 5/0083; A61F 5/0086; A61F 5/0089
USPC ................................................. 606/151, 232
See application file for complete search history.

(56) References Cited

U.S. PATENT DOCUMENTS

| 3,958,576 | A | * | 5/1976 | Komiya | 606/142 |
|---|---|---|---|---|---|
| 5,297,536 | A | | 3/1994 | Wilk | |
| 5,370,661 | A | * | 12/1994 | Branch | 606/232 |
| 5,372,146 | A | * | 12/1994 | Branch | 128/898 |
| 5,403,326 | A | * | 4/1995 | Harrison et al. | 606/139 |
| 5,458,131 | A | | 10/1995 | Wilk | |
| 5,626,614 | A | | 5/1997 | Hart | |
| 5,846,182 | A | | 12/1998 | Wolcott | |

(Continued)

FOREIGN PATENT DOCUMENTS

DE      198 27 255 A1   12/1998
DE  10 2008 025 456 A1  12/2008
(Continued)

*Primary Examiner* — Julian W Woo
*Assistant Examiner* — Shaun L David
(74) *Attorney, Agent, or Firm* — Woodard, Emhardt, Moriarty, McNett & Henry LLP

(57) ABSTRACT

Described, in certain embodiments, are methods and apparatuses for delivering anchoring devices such as T-anchors into body passage walls. Some inventive methods involve inserting one or more anchoring devices into a wall of an organ in a direction from a luminal surface to an abluminal surface of the wall. In some instances, inserting a device in this manner, while providing at least part of the device implanted between the luminal surface and the abluminal surface of the wall, is conducted without the device exiting the wall's abluminal surface. In these and other inventive methods, delivering an anchoring device into a body passage wall may involve manipulating the wall in some manner before, during and/or after placing the device in the wall. Various forms of manipulation are described in this regard.

19 Claims, 4 Drawing Sheets

(56) References Cited

U.S. PATENT DOCUMENTS

| | | | |
|---|---|---|---|
| 5,976,127 A * | 11/1999 | Lax | 606/32 |
| 6,030,365 A | 2/2000 | Laufer | |
| 6,491,714 B1 * | 12/2002 | Bennett | 606/232 |
| 6,581,974 B1 | 6/2003 | Ragner et al. | |
| 6,592,596 B1 * | 7/2003 | Geitz | 606/139 |
| 6,736,828 B1 * | 5/2004 | Adams et al. | 606/213 |
| 7,074,229 B2 * | 7/2006 | Adams et al. | 606/151 |
| 7,416,554 B2 * | 8/2008 | Lam et al. | 606/153 |
| 7,632,287 B2 * | 12/2009 | Baker et al. | 606/151 |
| 7,678,122 B2 * | 3/2010 | Kortenbach et al. | 606/142 |
| 7,704,264 B2 * | 4/2010 | Ewers et al. | 606/151 |
| 7,846,180 B2 * | 12/2010 | Cerier | 606/232 |
| 7,942,887 B2 * | 5/2011 | Kraemer et al. | 606/151 |
| 2003/0225312 A1 | 12/2003 | Suzuki et al. | |
| 2005/0075653 A1 * | 4/2005 | Saadat et al. | 606/139 |
| 2005/0075654 A1 * | 4/2005 | Kelleher | A61B 17/0401 606/151 |
| 2005/0080412 A1 | 4/2005 | Ouchi | |
| 2005/0187565 A1 * | 8/2005 | Baker et al. | 606/151 |
| 2005/0251206 A1 * | 11/2005 | Maahs et al. | 606/232 |
| 2006/0015125 A1 * | 1/2006 | Swain | 606/151 |
| 2006/0089660 A1 | 4/2006 | Saeed et al. | |
| 2006/0116735 A1 * | 6/2006 | Imran et al. | 607/40 |
| 2006/0259074 A1 * | 11/2006 | Kelleher et al. | 606/213 |
| 2007/0112362 A1 | 5/2007 | Mikkaichi et al. | |
| 2007/0112385 A1 | 5/2007 | Conlon | |
| 2007/0129735 A1 * | 6/2007 | Filipi et al. | 606/144 |
| 2007/0167675 A1 * | 7/2007 | Miyamoto et al. | 600/104 |
| 2007/0167676 A1 | 7/2007 | Miyamoto et al. | |
| 2007/0260112 A1 | 11/2007 | Rahmani | |
| 2010/0030243 A1 * | 2/2010 | Baker et al. | 606/151 |

FOREIGN PATENT DOCUMENTS

| | | |
|---|---|---|
| JP | 2000-300570 | 10/2000 |
| JP | 2002 330918 | 11/2002 |
| JP | 2006 325867 | 12/2006 |
| WO | WO 01/58360 A2 | 8/2001 |
| WO | WO 2007/059068 A1 | 5/2007 |

* cited by examiner

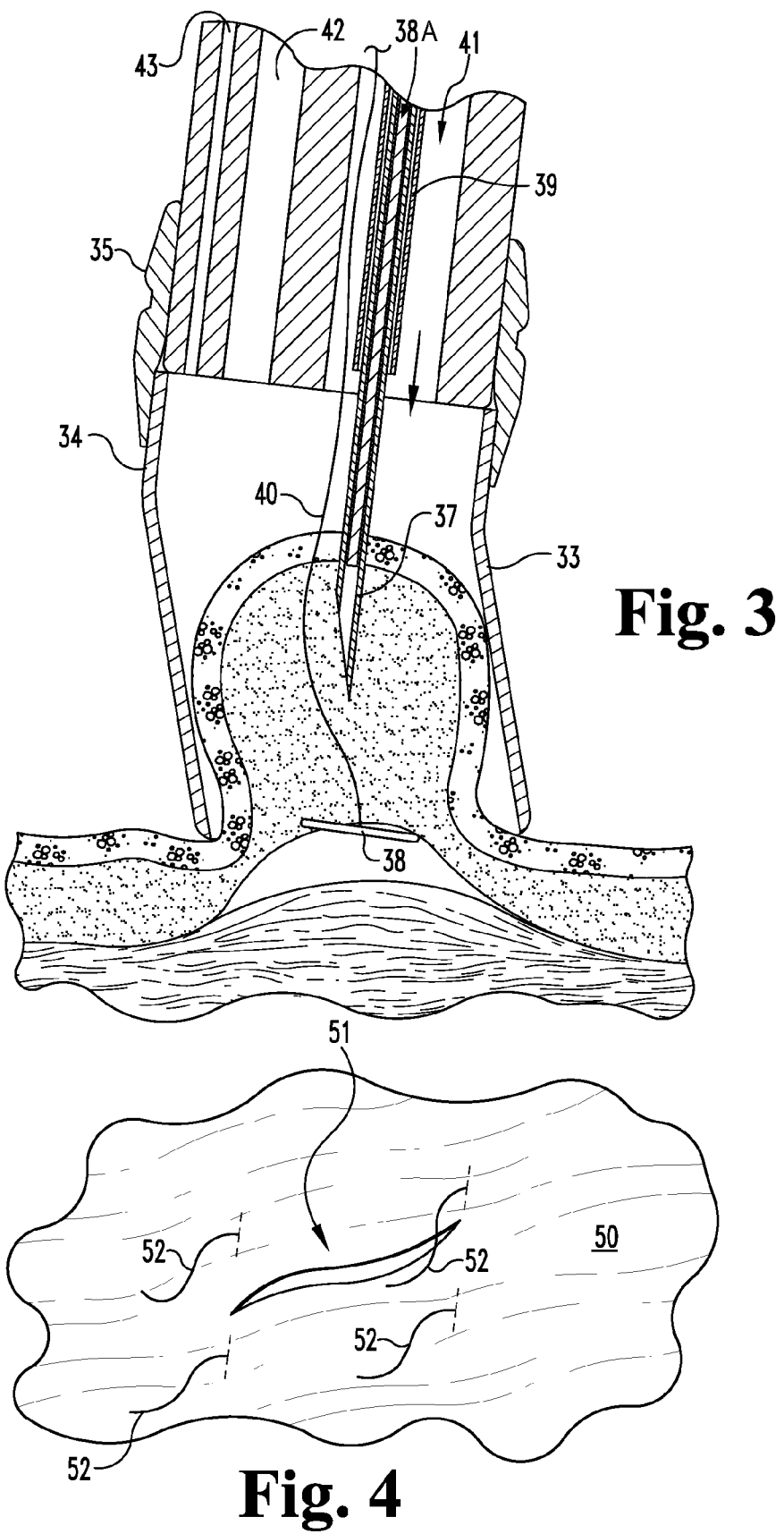

METHODS AND APPARATUSES FOR DELIVERING ANCHORING DEVICES INTO BODY PASSAGE WALLS

REFERENCED TO RELATED APPLICATIONS

This patent application claims the benefit of U.S. Provisional Patent Application No. 60/992,508, filed Dec. 5, 2007, which is incorporated by reference herein in its entirety.

BACKGROUND

The present invention relates generally to medical technology and in particular aspects to methods and apparatuses for delivering anchoring devices into body passage walls.

As further background, anchoring devices such as T-anchors may be delivered into walls of a hollow organ or other body structure for a variety of reasons. Often, an anchoring device will be employed to anchor or at least help anchor another object in the body, for example, another anchoring device or an endoluminal gastrointestinal device such as but not limited to an artificial stoma device, a gastrointestinal bypass sleeve device or an attachment cuff. Additionally or alternatively, an anchoring device may be placed in a body passage wall in an effort to close an opening in the wall or otherwise secure portions of the wall together.

An opening may be present in a body passage wall for a variety of reasons, for example, as a result of disease or an intentional or unintentional trauma. In performing some medical procedures, an opening is intentionally created in a body lumen wall, for example, from within the lumen to provide access to a region of the body occurring beyond the lumen wall. This category of procedures includes NOTES (Natural Orifice Transluminal Endoscopic Surgery). During NOTES, a flexible endoscope or other similar instrument is used to create a transvisceral incision via natural orifice access to enter the peritoneal cavity where a variety of medical procedures including but not limited to diagnostic exploration, gastric bypass, liver biopsy, oophorectomy, cholecystectomy, appendectomy, splenectomy, and fallopian tubal ligation can be performed. Following the intervention, the scope is pulled back through the opening, and the opening is closed.

While minimally invasive access to the abdominal cavity is required for a variety of diagnostic and therapeutic purposes in the medical field, until recently, such abdominal access has required a formal laparotomy to provide sufficient exposure. NOTES can provide an alternative or supplement to other types of surgery. It eliminates abdominal incisions and incision-related complications by combining endoscopic and laparoscopic techniques to diagnose and treat abdominal pathology. Common incision-related complications such as wound infections, incisional hernias, postoperative pain, aesthetic disdain, and adhesions can be minimized or eliminated by NOTES.

There remain needs for improved and/or alternative methods and apparatuses for delivering anchoring devices and other similar objects into body passage walls. The present invention is addressed to those needs.

SUMMARY

The present invention provides, in certain aspects, unique methods and devices for delivering anchoring devices into patient tissues. One illustrative method involves delivering an anchoring device into a wall of the alimentary canal where the wall has a luminal surface and an abluminal surface. In this method, an anchoring device is provided and then inserted into the wall in a direction from the luminal surface to the abluminal surface. This insertion is conducted such that the anchoring does not exit the abluminal surface, and provides the anchoring device implanted within the wall structure between its luminal surface and abluminal surface.

Another embodiment of the present invention provides a medical apparatus for delivering an anchoring device into a wall of a body passage. This medical apparatus comprises an endoluminally advanceable device, which is configured to apply suction to a luminal surface of a body passage wall to provide an inwardly displaced volume of tissue. Additionally, the product includes an anchoring device that is cooperable with the endoluminally advanceable device, and is deliverable into the inwardly displaced volume of tissue.

Another embodiment of the invention provides a medical kit for equipping an endoluminally advanceable device, such as an endoscope, for delivery of an anchoring device into patient tissue. The endoluminally advanceable device has an operating channel and is configured to deliver suction through an opening at or proximate to a distal end of the operating channel. The kit includes a barrel for receipt upon the distal end of the endoluminally advanceable device. The barrel is configured to receive suction from the operating channel so as to draw patient tissue into the barrel. The kit further includes an anchoring device deliverable through the working channel and implantable in patient tissue that is drawn into the barrel. In certain embodiments, the barrel is a modified barrel that includes a proximal segment and a distal segment extending at an offset angle from the proximal segment. Such modified barrels can be configured for mounting on the end of an endoscope or other endoluminally advanceable device, with the proximal segment in alignment with the body of the advanceable device. In this fashion, the distal barrel segment will be positioned at an offset angle relative to the distal body of the advanceable device.

In another embodiment, the invention provides a method for delivering an anchoring device into a wall of a body passage. In one step, suction is applied to a luminal surface of the body passage wall where in doing so a portion of the wall is displaced toward an interior region of the body passage. In another step, an anchoring device is passed through the luminal surface of the displaced wall portion and through at least part of the body passage wall.

One aspect of the present invention provides a method for delivering an anchoring device into a wall of a body passage. In this method, an anchoring device and a tissue displacing device are provided. In one step, the body passage wall is manipulated with the tissue displacing device such that the wall is displaced toward an interior region of the body passage. This manipulating is conducted without penetrating the body passage wall. In another step, the anchoring device is passed through the luminal surface and through at least part of the body passage wall.

Another aspect of the invention provides a method for delivering an anchoring device into a wall of a body passage. This method includes providing an anchoring device and an endoluminally advanceable device that includes a tissue receiving chamber. In one step, a volume of tissue is received in the tissue receiving chamber. In another step, the anchoring device is inserted into the volume of tissue.

A further embodiment of the invention provides a method for delivering an anchoring device into a wall of a body passage. One step includes providing an anchoring device. In another step, force is applied to a luminal surface of the body passage wall where in doing so the wall is displaced toward an interior region of the body passage. In another step, the anchoring device is passed through the luminal surface and toward an abluminal surface of the body passage wall. This passing is conducted such that the anchoring device does not exit the abluminal surface, and provides the anchoring device implanted between the luminal surface and the abluminal surface.

Other objects, embodiments, forms, features, advantages, aspects, and benefits of the present invention shall become apparent from the detailed description and drawings included herein.

BRIEF DESCRIPTION OF THE DRAWINGS

FIGS. 2-3 depict steps of one illustrative inventive method and components of inventive devices and apparatuses.

FIG. 4 depicts a plurality of anchors implanted in a body wall useful for closure of an incision or other opening in the wall.

DETAILED DESCRIPTION

Figure 1:
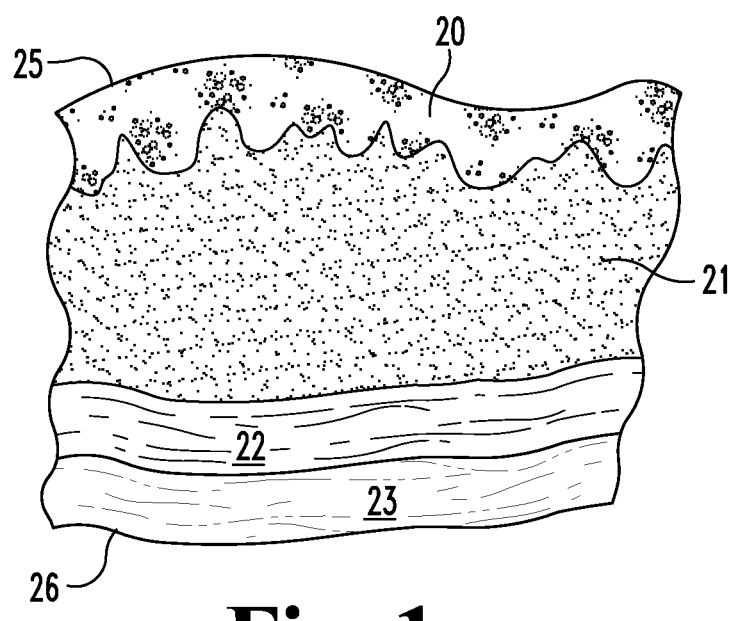
FIG. 1 is a cross-sectional view of a wall of the alimentary canal.

While the present invention may be embodied in many different forms, for the purpose of promoting an understanding of the principles of the present invention, reference will now be made to the embodiments illustrated in the drawings, and specific language will be used to describe the same. It will nevertheless be understood that no limitation of the scope of the invention is thereby intended. Any alterations and further modifications in the described embodiments and any further applications of the principles of the present invention as described herein are contemplated as would normally occur to one skilled in the art to which the invention relates.

As disclosed above, in certain aspects, the present invention provides unique methods and apparatuses for delivering anchoring devices into bodily structure walls. Illustratively, some inventive methods involve inserting one or more anchoring devices into a wall of an organ in a direction from a luminal surface to an abluminal surface of the wall. In some instances, inserting a device in this manner, while providing at least part of the device implanted between the luminal surface and the abluminal surface of the wall, is conducted without the device exiting the wall's abluminal surface. Additionally, in these and other inventive methods, delivering an anchoring device into a body passage wall can involve manipulating the wall in some manner before, during and/or after placing the device in the wall. Various forms of manipulation are contemplated in this regard. Illustratively, a desirable manipulation can involve repositioning or otherwise displacing tissue of a wall prior to inserting an anchoring device. In some preferred embodiments, a portion of an organ wall is forced in a direction opposite to the direction in which the anchoring device is to be forcibly inserted, e.g. to some extent toward an interior region of the organ (e.g., using suction and/or other force), and thereafter, an anchoring device is delivered into this portion of the wall. In instances where an anchoring device is inserted into displaced organ wall tissue in a direction from a luminal surface to an abluminal surface of the wall, the insertion may or may not be conducted with the device exiting the abluminal surface.

Anchoring devices can be delivered into a variety of bodily structures in accordance with the present invention. These structures, in some preferred embodiments, will be a wall of a hollow organ or other body passageway. A wall of this sort will typically have a luminal surface comprised of mucosa or a mucosa-like tissue, and an abluminal surface comprised of serosal tissue. An alimentary canal wall will provide a suitable site for implanting one or more anchoring devices in accordance with certain embodiments of the present invention. Referring to FIG. 1, there is illustrated a section of an alimentary canal wall showing a mucosa layer 20, a submucosa layer 21, a muscle layer 22 and an adventitia or serosa layer 23. In this regard, the wall is considered to have a luminal surface 25 and an abluminal surface 26.

When an anchoring device is delivered into a body passage wall in accordance with the present invention, it can be placed at any suitable location in and along the wall. Thus, anchoring devices can be placed at a variety of locations along an alimentary canal wall, e.g., in regions including the esophagus, stomach and/or intestines. As well, when placing an anchoring device in a wall, it can be placed at various depths in the wall. As will be discussed in more detail hereinbelow, an anchoring device, upon delivery, can be located entirely within the body passage wall, or alternatively, it can have portions extending beyond the wall in the luminal and/or abluminal direction.

Anchoring devices used in aspects of the invention will be configured to provide some sort of anchoring or retention capability in the body, for example, for securing or otherwise holding tissue in a desirable position in the body and/or for anchoring or retaining another object in the body such as but not limited to another retention or anchoring device (e.g., a suture), an endoluminal gastrointestinal device such as an artificial stoma device, a gastrointestinal bypass sleeve device or an attachment cuff, etc. Illustratively, an anchoring device can be adapted for delivery to a site in the body, and then once at that site, can be effective to generally maintain its position there, even when considerable forces are applied to the device to remove it from the site.

In some preferred embodiments, an anchoring device will include at least one anchoring surface for directly or indirectly contacting tissue of a body passage wall to maintain or at least help maintain the anchoring device at a desirable location in and/or around the wall. An anchoring surface may be shaped and configured in a variety of manners, for example, including planar and/or non-planar surface portions. In some embodiments, an anchoring surface will have features that are rounded or otherwise curvilinear.

Anchoring devices useful in some aspects of the invention will incorporate one or more adaptations useful to secure or otherwise connect the anchoring device to patent tissue and/or another object or material in the body. Such a component may comprise an anchoring surface such as that described above. In some preferred embodiments, an adaptation of this sort will be a stem or other elongate element that extends generally away from other parts of the anchoring device. A stem or other similar adaptation may be comprised of any of a variety of objects or materials such as but not limited to a single strand or multi-strand filament or other material, e.g., a suture. A particular material may be selected to take advantage of one or more of its properties such as but not limited to its weight, durability, flexibility, etc. Illustratively, an anchoring device, or selected portions thereof (e.g., a stem portion), can exhibit a degree of flexibility. In this regard, parts of an anchoring device may be rigid, malleable, semi-flexible, or flexible.

An elongate element and other portions of an anchoring device may be formed together as a single unit, or alternatively, an elongate element may be formed separately and then combined with other portions of an anchoring device, for example, with an adhesive, by welding, using mechanical fastener(s), and/or any other suitable joining means. In some preferred forms, an anchoring device will comprise an anchoring surface that extends in a generally lateral direction with respect to a longitudinal axis of an elongate element (e.g., a suture, staple, stem, rivet, etc.) that extends generally away from the anchoring surface.

In some aspects, an anchoring device is equipped such that during a placement procedure the surface area available for contacting patient tissue for anchoring purposes can be caused or allowed to increase. In some embodiments, this increase will involve the movement of one or more device portions relative to other parts of the device, for example, when a device employs a hinged component or otherwise involves a repositioning of one or more device portions (e.g., an anchoring surface). Configurations of this sort can allow a device to have a relatively lower profile in the direction of insertion for delivery purposes (for deployment through a deployment needle or other delivery device cannula and/or travel through a tissue tract or other opening, etc.). Illustratively, an anchoring device, such as a T-anchor, can include an anchoring surface configurable to a first orientation enabling the device to pass through a narrow tissue tract in patient tissue, and a second orientation for inhibiting the passage of the anchoring device back through the tissue tract. Such a surface can be caused or allowed to reposition in a variety of manners, for example, by pivoting the anchoring surface.

The manner in which an anchoring device is inserted or otherwise delivered into a volume of tissue can vary in accordance with the present invention. In some embodiments, an anchoring device is delivered into a volume of tissue using a needle, cannula or other suitable delivery instrument, for example, with all or part of the anchoring device positioned in a bore, lumen, recessed area or other open space in the needle. While not necessary to broader aspects of the invention, an anchoring device can be directly or indirectly received in or attached to a delivery instrument, for example, in a releasable fashion. In some instances, anchoring devices are adapted to be carried within an internal cannula of a delivery needle or other instrument for delivery into tissue. Delivery with the aid of these and other delivery instruments can involve pushing and/or pulling an anchoring device through tissue. In instances where an anchoring device incorporates a tether or other elongate element (e.g., a suture), this element can extend along a needle or other instruments used to deliver the anchoring device, or alternatively, all or part of the tether can reside in the needle (e.g., extending through a central cannula in the needle).

Some aspects of the invention involve manipulating the orientation or positioning of a body passage wall as part of delivering an anchoring device into the wall. Such a manipulation, in some embodiments, may be effective to lower the risk of causing unintended injury to other body parts in the vicinity of the wall. A manipulation of this sort can include, for example, forcing a wall of the passage in a direction that is substantially opposite to the direction of force to be used to insert the anchoring device, and/or causing a portion of a wall to move generally toward an interior region of the lumen. Moving or displacing a wall in this manner can be accomplished in a variety of fashions such as by applying various forms of force to the wall as described elsewhere herein. A procedure can involve the application of mechanical and/or non-mechanical force to a wall. When a manipulation is to be performed, it will typically be initiated before an anchoring device enters the wall and then maintained throughout the insertion process, although other suitable times and durations of manipulation are contemplated as within the scope of the present invention. As discussed elsewhere herein, these and other inventive apparatuses and methods can involve a tubular surgical access device equipped with (or otherwise usable in conjunction with) suitable direct or indirect (e.g. imaging) visualization means.

In certain preferred embodiments, displacing a portion of a body lumen wall (e.g., toward an interior region of the lumen) involves applying suction to the luminal surface of the wall. Inventive apparatuses and methods utilizing suction may be particularly useful in situations where it is desirable to inflict as little damage to the surrounding tissues as possible. In some aspects of the invention, a portion of an organ wall is drawn inwardly to some extent by applying suction to a luminal surface of the wall, and thereafter, an anchoring device is delivered into a region of the wall that includes this inwardly drawn portion. A variety of devices can be utilized to provide suction in the body, for example, those involving a hollow, tubular device having a vacuum source connected to its proximal end. Although not necessary to broader aspects of the invention, endoscopic equipment and techniques can be employed in this regard to displace tissue that is targeted for accepting one or more anchoring devices in accordance with the present invention, for example, to prevent or at least minimize the risk of an anchoring device exiting the abluminal surface of a wall and damaging surrounding bodily structures.

Certain aspects of the invention involve a device that is effective to displace tissue of a body passage wall, while additionally providing a chamber or other open space into which a volume of the displaced tissue (e.g., mucosal and submucosal tissue) can be received. Inventive apparatuses and methods in this vein may or may not involve the application of suction to the tissue to be displaced. Additionally or alternatively, tissue can be mechanically drawn or otherwise brought into a chamber or other space in a device.

In some preferred embodiments, a barrel or other similar device component such as those often used in tissue ligation procedures can be affixed to the end of an endoscope, and suction can be used to draw an amount of tissue into the barrel. In some forms, such a device will also be equipped with a needle or other suitable delivery instrument, which is receivable through an operating channel of the device (e.g., an endoscope), and is effective to deliver one or more anchoring devices through the chamber and into the volume of displaced tissue, although delivery instruments passed separately and/or outside of the endoscope may be employed as well.

In inventive embodiments that involve receiving tissue of a body passage wall in a barrel or other similar space that is designated for receiving such tissue, and then delivering of an anchoring device into this tissue, highly precise and controlled delivery outcomes can be achieved. In certain embodiments, a barrel is provided with calibrations inside of the barrel that are visible to the physician endoscopist, so that the amount of captured tissue can be determined. In this manner, the endoscopist can estimate the depth that the anchoring device will travel into the tissue wall.

Figure 2:
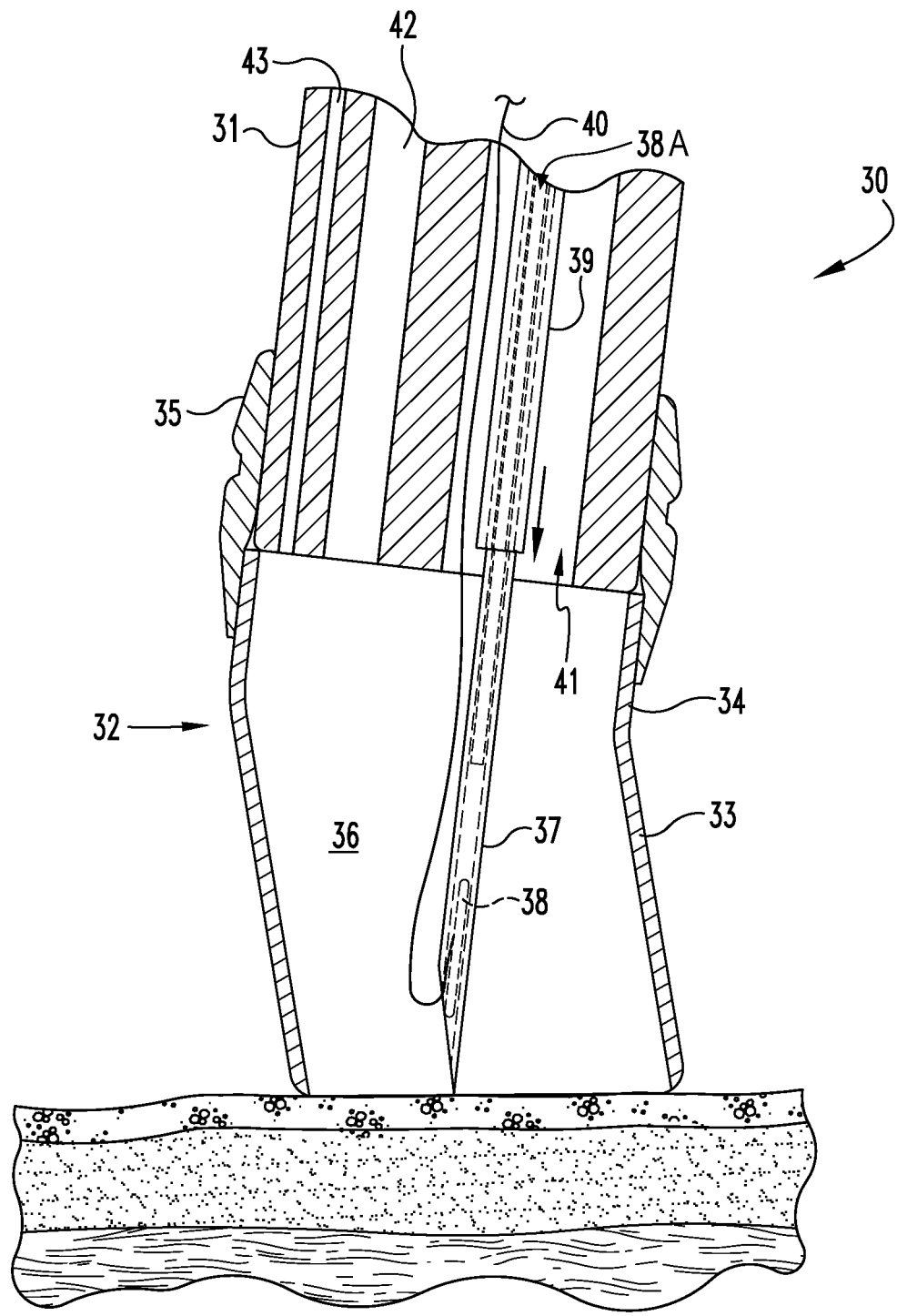
Figure 5:
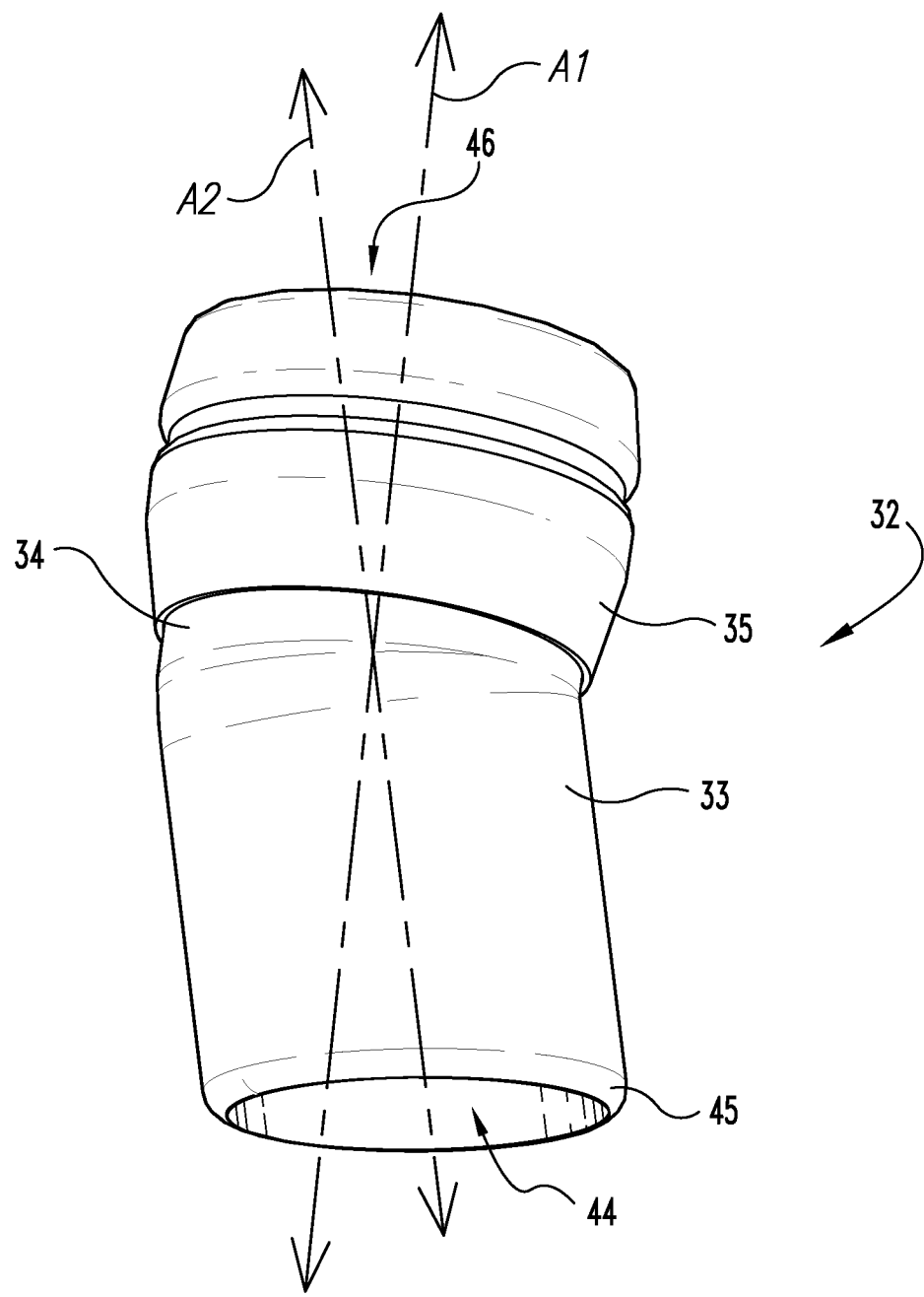
FIG. 5 provides a perspective view of an illustrative barrel implement of the invention.

With reference now to FIG. 2, shown is an inventive apparatus 30 that utilizes suction to displace patient tissue. Apparatus 30 includes an endoluminally advanceable device such as an endoscope 31 and a barrel implement 32 disposed on the distal end of the endoscope 31. Barrels such as that shown in FIG. 2 can facilitate the capture and presentation of tissue at preferred angles relative to the endoscope 31, although it will be understood that a variety of other beveled and non-beveled barrels may be utilized as well. With reference now to FIG. 5 as well, barrel 32 includes a first segment 33 and a second segment 34, wherein the longitudinal axis A1 of segment 34 is at an offset angle "θ" relative to the longitudinal axis A2 of segment 33. Offset angle θ can be any suitable angle, including for instance from about 1 degree to about 45 degrees, more typically from about 3 degrees to about 15 degrees. In one preferred embodiment, offset angle θ is about 10 degrees. In this manner, utilizing flexible hub 35, the proximal open end 46 of the barrel 32 can be mounted on the distal end of endoscope 31 with the longitudinal axis A1 of segment 34 substantially aligned with the longitudinal axis of the distal end of the endoscope, and the longitudinal axis A2 of the distal segment 33 will then reside at an offset angle both from the axis A1 of proximal barrel segment 34 and the longitudinal axis defined by the distal end of endoscope 31. Accordingly, the axis A2 of the barrel segment 33 can be at an offset angle relative to the axis of the distal end of the endoscope (and to the axis of the distal end of operating channel) equivalent to the values given for θ above. As will be discussed more fully below, this can facilitate an advantageous angle of approach when surgically accessing tissue drawn into the interior region 36 of barrel 32.

In some inventive methods, the distal end 45 of the barrel can be beveled, and the distal opening 44 of barrel 32 can be positioned against or near a luminal surface of a body passage wall such as that depicted in FIG. 1, and suction can be provided in the barrel 32, causing a portion of the wall to be drawn into the distal open end of barrel 32. In certain embodiments, the captured tissue includes mucosal and submucosal tissue, with some muscle tissue positioned at or near the distal open end of barrel 31. Depending on a number of factors including but not limited to the size of the barrel, magnitude of the suction, characteristics of the tissue being suctioned, etc., the amount and type of tissue received in the barrel can vary. An anchoring device can be delivered into (and at least partially through) a volume of captured tissue such as that shown in FIG. 2. Illustratively, one or more anchoring devices can be passed through a working channel of the endoscope and forced into the captured tissue, for example, with the aid of a needle or other similar delivery instrument, although any suitable manner of directly or indirectly forcing an anchoring device into the displaced tissue may be utilized such as with a spring-loaded or pneumatic firing mechanism.

FIG. 2 also illustrates the combination of the endoscope 31 and barrel 32 with a T-anchor delivery assembly. The T-anchor delivery assembly includes a cannulated needle 37 having the end piece 38 of a T-anchor device received in the distal portion of its cannula. Needle 37 is received through a catheter or sheath 39. The suture 40 of the T-anchor device passes out of the needle 37 and runs along the outside of sheath 39 as illustrated. The suture 40 is attached to the end piece 38 and extends back through the endoscope 31 desirably to a location outside of the body when end piece 38 is implanted inside the body. A pusher bar 38A is positioned within the cannula of needle 37 and is slidable therein so as to enable pushing and deploying end piece 38 from needle 37 at an appropriate point in the procedure.

The T-anchor delivery assembly is introduced through the operating channel 41 of endoscope 31. Operating channel 41 is in fluid communication with a vacuum source. Endoscope 31 may have other channels 42 and 43 therethrough as is conventional, for example to advance optical fibers or other lighting implements, to advance or hold video cameras and power and/or signal feeds thereto and therefrom, or to provide other functions to endoscope 31.

FIGS. 2 and 3 together illustrate a method in which the apparatus 30, with the combined T-anchor delivery assembly, can be used to insert a T-anchor in patient tissue. In one mode of practice, as shown in FIG. 2, needle 37 can be advanced within the barrel 32 into but not beyond its distal end. This process can be endoscopically visualized. As illustrated, with distal barrel segment 33 at an offset angle relative to the endoscope 31, and with the endoscope having a non-centrally-located working channel 41, barrel 32 can be positioned on endoscope 31 such that needle 37 or other instruments exiting channel 41 will extend from a position closer to the side wall of segment 33 to a position more central within segment 33 as the needle 37 or other instrument is advanced distally within barrel 32. In the illustrated embodiment, this is accomplished by positioning the barrel 32 so that the longitudinal axis A2 of the distal barrel segment 33 intersects the longitudinal axis of the distal-most portion of the working channel 41, with that intersection occurring at a point distal of the distal end of the endoscope 31. Then, suction can be applied through working channel 41 thus drawing patient tissue into the interior region 36 of the barrel 32. In doing so, the needle 37 will be caused to penetrate the tissue as it is drawn into the interior region 36 of barrel 32. In certain embodiments, the tissue drawn into the barrel does not include the entire wall of the stomach or another alimentary wall structure, and thus the needle 37 penetrates only partially through the wall. In this regard, the needle can penetrate mucosa 20 and submucosa tissue 21, but not muscle tissue 22 underlying the submucosa tissue. Such a procedure enables implanting the end piece 38 of the T-anchor device generally underneath the submucosa tissue 21, but not beyond the muscle tissue 22. With the needle penetrating the wall to the desired depth, the pusher bar 38A is used to deploy the end piece 38 from the needle 37. As illustrated, in certain embodiments, the end piece 38 will be anchored into or just beneath the submucosal tissue 21 within the wall. It has been discovered that such implanted T-anchor devices exhibit a robust anchoring function, strong enough for a variety of tissue manipulations including suturing, repositioning, and others. After deploying the T-anchor end piece 38, the needle 37 can be removed from the displaced tissue by terminating the suction through channel 41 and/or by manually withdrawing needle 37 upwardly into barrel 32 and eventually back into channel 41. While the above passages describe steps in one method for implanting the T-anchor using apparatus 30, other steps and methods are also contemplated as being within the invention. Illustratively, rather than applying suction to displace tissue against and over the pre-advanced needle 37, suction can first be applied to displace tissue, and then needle 37 can be advanced into the already-displaced tissue. Combinations of these operations can also be used in order to achieve penetration of the needle into the tissue. In all of these operations, in one mode of practice, the distal end of the needle 37 can be maintained aligned with or proximal to the distal end 44 of barrel 32. In this manner, increased protection is provided against the needle 37 inadvertently penetrating organs or tissues adjacent to an organ wall undergoing surgical manipulation.

A delivery instrument such as needle 37 can be used to deliver an anchoring piece, for example end piece 38, to various depths in tissue wall or other bodily structure. Thus, while anchoring piece 38 is shown in FIG. 3 at or near the transition area between submucosal tissue 21 and muscle tissue 22, it will be understood that the device could be advanced to other suitable locations in the wall. Additionally, although FIG. 3 shows delivery needle 37 delivering a single anchoring device, it will be understood that this and other similar delivery instruments useful in the invention can be adapted to deploy any suitable number of anchoring devices, and in some instances, will house one to ten or more anchoring devices, more typically two to eight anchoring devices.

The implanted anchoring device may be the same or similar to devices commonly referred to as T-tags, T-fasteners, T-anchors, etc. Such devices will generally be in the shape of a "T", and can be described as including a flexible tether extending from a crossbar portion. When a T-anchor includes a crossbar portion, the crossbar portion can vary in size, for example, having a length ranging from about 0.4 mm to about 4.0 mm, more typically from about 1 mm to about 2.5 mm.

As noted above, anchoring devices can be placed at various depths in a body passage wall in accordance with the present invention. Lumen walls of body passageways such as the esophagus, stomach and intestines generally include a mucosal layer and an underlying submucosal connective tissue layer, commonly followed by a muscular layer and then a serosal layer. In some embodiments, an anchoring device will be implanted so that a substantial portion of the device resides in tissue that occurs to the luminal side of a discernable serosal layer, and in some cases, to the luminal side of a discernable muscular layer of the passageway wall. In certain aspects of the present invention, an open space is created within a body passage wall for receiving all or part of an anchoring device. Illustratively, fluids (e.g., saline) can be injected or otherwise delivered into a tissue wall to create such an open space.

Additionally or alternatively, mechanical and/or non-mechanical forces as described herein can be applied to a body passage wall in an effort to create an open volume into which all or part of an anchoring device can be placed. Providing this sort of space may occur in conjunction with amounts of tissue being displaced toward an interior region of the body passageway. In some instances, space can be created generally between submucosal and muscle tissue. In this regard, it is known that the connective tissue of submucosal layers often interleaves with amounts of muscle tissue, especially but not exclusively in areas transitioning from histologically-identifiable submucosa layers to underlying muscle layers.

Anchoring devices such as T-anchors may be delivered into walls of a hollow organ or other body passage for a variety of purposes. Often, an anchoring device will be employed to anchor or at least help anchor another object in the body, for example, another anchoring device or an endoluminal gastrointestinal device such as but not limited to an artificial stoma device, a gastrointestinal bypass sleeve device or an attachment cuff. Additionally or alternatively, an anchoring device may be placed as a suture in a body passage wall in an effort to close an opening in the wall or otherwise secure portions of the wall together. For instance, an anchoring device may be connected to one or more other anchoring devices, for example by one or more suture(s) and/or clips or the like, to hold an opening in a tissue wall closed to promote and/or facilitate closure and healing of the opening.

Methods and apparatuses of the invention find particular use in the closure of incisions or other openings occurring in a body lumen wall, regardless of the cause of the opening, and whether the opening extends fully or partially through the lumen wall. An opening of this sort may be caused, for example, by disease or by an intentional or unintentional trauma. In some instances, an opening in a body lumen wall will be created from within the lumen to provide access to a region of the body occurring beyond the lumen wall. Illustratively, an opening may be created in a wall of the gastrointestinal tract, bladder, colon, vagina, etc., to access an intra-abdominal region. Thus, using endoscopic instrumentation, the wall of the lumen (e.g., the stomach) can be punctured, and an endoscope can be advanced into the peritoneal cavity to perform various procedures including but not limited to diagnostic exploration, gastric bypass, liver biopsy, oophorectomy, cholecystectomy, appendectomy, splenectomy, and fallopian tubal ligation. After the intervention is finished, the scope is pulled back into the body lumen through the opening. Other natural orifices, such as the anus, urethra, nose or vagina, may also allow access to the peritoneal cavity. While not necessary to broader aspects of the invention, an opening to be closed may have been created to perform NOS (Natural Orifice Surgery) or NOTES (Natural Orifice Transluminal Endoscopic Surgery).

FIG. 4 shows a tissue wall 50 that includes an opening 51 in part of the wall. This sort of opening may be present in a wall of a bodily structure for a variety of reasons, for example, as a result of disease or an intentional or unintentional trauma. In performing some medical procedures, an opening such as opening 51 will be intentionally created in a body lumen wall, for example, as may occur in a NOTES procedure. In an attempt to close or otherwise modify opening 51, a plurality of anchoring devices may be delivered into wall 50 as described elsewhere herein. Each anchoring device provides a suture 52. Sutures or other elongate elements extending into a body lumen can extend out of the lumen, or alternatively, can terminate there such as by tied knots, sliding buttons or clips, or preexisting terminated ends, such that they would not need to be brought outside of the body. Thus, as will be understood by those skilled in the art, each suture can be tied or otherwise fixed to one or more other sutures present and/or patient tissue to modify the opening, and in some cases, substantially close the opening. This specific illustrative embodiment shows one pattern of placing anchoring devices around an opening. A lesser or greater number of anchoring devices and/or sutures may be employed in other embodiments. As well, an anchoring device may be placed at any suitable location in a wall relative to an opening and/or another anchoring device.

In additional embodiments, the present invention provides kits that include means or devices as described herein for delivering anchoring devices into body passage walls, and written materials including instructions for use of the means or devices to deliver anchoring devices into body passage walls, e.g. in performing NOTES as described herein. The kits can include the means or devices packaged together with the instructions, e.g. in sterile medical packaging. Related embodiments of the invention include methods for distributing such means or devices, or otherwise conducting business, which include distributing such means or devices for delivering anchoring devices into body passage walls, and also distributing information relating the use of such means or devices for delivering anchoring devices into body passage walls. Such information can be distributed packaged with the means or device, or separately, e.g. including information or instructions available on a communication network, including a global computer communication network such as the internet.

The present invention also provides, in certain aspects, a line of medical products, wherein a medical product of the invention includes one or more devices, apparatuses or systems of the invention in a sealed package. In some forms of the invention, medical products are provided that include one or more anchoring devices such as any of those described herein, and potentially also a suitable delivery apparatus or other delivery instrumentation, enclosed within sterile medical packaging. Illustratively, such a medical product can have packaging including a backing layer and a front film layer that are joined by a boundary of pressure-adhesive as is conventional in medical packaging, wherein the contents of the packaging are sealed between the backing layer and front film layer. Sterilization of such a medical product may be achieved, for example, by irradiation, ethylene oxide gas, or any other suitable sterilization technique, and the materials and other properties of the medical packaging will be selected accordingly.

Additionally, the package can include indicia to communicate the contents of the package to a person, machine, computer, and/or electronic device. Such indicia may include the dimensions of, the type of materials used to form, and/or other useful information regarding the contents of the package. In certain embodiments, the contents are packaged for sale with instructions for use. For example, in certain preferred embodiments, a medical product includes at least one anchoring device and delivery instrumentation sealed within a sterile package, wherein the packaging can have visible indicia identifying the contents as suitable for closing an opening in a wall of tissue, and/or can contain or otherwise be associated with printed materials identifying the contents as such and including information concerning their use.

For the purpose of promoting a further understanding of certain aspects of the invention, the following Experimental is provided. It will be understood that this Experimental is intended to be illustrative and not limiting of the invention.

Example 1

Summary

In this Example, ovariectomy procedures were performed in cadaver dogs and in live dogs (canine hounds, 20 to 30 kg) via a NOTES (natural orifice transluminal endoscopic surgery) approach. Closure of a surgical incision in the stomach used in the NOTES procedure was closed using methods and devices of the invention.

Procedures:

NOTES procedures were performed first on four canine cadavers. Using a dual-channel, flexible endoscope to examine the inside of the stomach, access was created to the abdominal cavity using a guide wire, needle knife electrode, and balloon dilation catheter. The peritoneal cavity was inflated with air and techniques were developed for obtaining visualization and maintaining orientation to allow identification of abdominal structures. An electrocautery snare was placed around the ovarian tissue and activated to cut and coagulate the tissue. The tissue was then removed via the gastric incision. The gastrotomy was then closed using T-fastener devices implanted within the gastric wall adjacent the incision using techniques generally as described in FIGS. 1-5. Four T-fasteners were used, two implanted on each side of the incision. A clip was used to secure the two suture strands from a first opposed pair of T-fasteners. Another clip was similarly used to secure together the suture strands from a second opposed pair of the T-fasteners. In this fashion, successful apposition of the opposite sides of the incision was achieved.

Following the canine cadaver work, similar NOTES procedures were performed in five live dogs. Following anesthesia, an endoscope was passed and the stomach was examined to ensure that there were no free food particles. The stomach was lavaged with sterile water until clear and then cefazolin (1 g in 200 ml normal saline) was instilled and left in the stomach for 20 minutes. The antibiotic solution was then aspirated through the endoscope. An overtube was used to reduce oral contamination. A therapeutic endoscope was passed into the stomach. The gastrotomy site was chosen on the ventral (anterior) aspect of the stomach as close as possible to the greater curvatures with good transillumation and impression similar to gastrotomy tube placement techniques. An 18G catheter was inserted into the stomach and the trocar jagwire was inserted into the stomach and pulled into the scope. The guide wire was used as a guide for the needle knife to create the initial gastrotomy. The guidewire was then advanced and looped in the peritoneal cavity. A 20 mm endoscopic balloon dilator was then passed over the guide wire and used to dilate the initial gastrotomy. The endoscope was positioned at the back of the balloon and the endoscope and balloon passed through the gastrotomy into the opening in the peritoneal cavity. Insufflation with room air was provided via the endoscope to create an optical space for viewing the abdominal structures. The animal was rotated and tilted to expose one of the ovaries. An endoscopic snare was passed through one of the working channels of the endoscope and used to grasp and elevate the ovary. A second endoscopic grasping forceps was inserted through the second working channel and used to elevate the ovary and assist in positioning the loop. The suspensory ligament, ovarian pedicle, and fallopian tube were identified. Monopolar electrocautery was used to coagulate and cut these structures. The site was then examined for hemorrhage. The ovary was then removed by holding it with the endoscopic grasping forceps or snare and removing the endoscope, keeping the guide wire in place. The endoscope was reintroduced over or adjacent to the guide wire into the peritoneal cavity. The animal was then rotated to the opposite side and the procedure was repeated on the left ovary. The gastrotomy was closed with four T-fasteners and two surgical clips as described for the cadaver work above. Necropsy evaluation was performed 10 days following surgery to assess the operative site. The evaluation demonstrated that all sites were healing as expected. There was no evidence of peritonitis in any of the dogs, or any other complications related to the T-fasteners or closure technique.

The animals utilized in this study were handled and maintained in accordance with the requirements of the Animal Welfare Act (9CFR Parts 1&2) and its amendments. Compliance was accomplished by conforming to the standards promulgated in the Guide for the Care and Use of Laboratory Animals, 1996 (NCR, ILAR, and National Academy Press).

All publications and patent applications cited in this specification are herein incorporated by reference as if each individual publication or patent application were specifically and individually indicated to be incorporated by reference. Further, any theory, mechanism of operation, proof, or finding stated herein is meant to further enhance understanding of the present invention, and is not intended to limit the present invention in any way to such theory, mechanism of operation, proof, or finding. While the invention has been illustrated and described in detail in the drawings and foregoing description, the same is to be considered as illustrative and not restrictive in character, it being understood that only selected embodiments have been shown and described and that all equivalents, changes, and modifications that come within the spirit of the inventions as defined herein or by the following claims are desired to be protected.

What is claimed is:

1. A method of delivering an anchoring device into a wall of a body passage from an endoluminally advanceable device comprising a tissue receiving chamber having a distal opening, the method comprising:
   providing an anchoring device having an anchor member and an elongate flexible element attached to the anchor member;
   applying suction to a luminal surface of the body passage wall through the endoluminally advanceable device and into the chamber so as to create a pseudopolyp of tissue that is displaced toward an interior region of the body passage through the distal opening and into the chamber, said pseudopolyp of tissue constituted of tissue of a segment of the body passage wall aligned with said distal opening, and said pseudopolyp of tissue constituted of only a portion of a thickness of said segment of the body passage wall so as to leave an abluminal surface of said segment of the body passage wall positioned exterior of the chamber;
   implanting the anchor member of said anchoring device completely within the body passage wall which includes inserting said anchor member into said pseudopolyp of tissue by delivery from a delivery instrument inserted only partially through the body passage wall;
   leaving the anchor member of the anchoring device implanted completely within the body passage wall with the anchoring device having not exited the abluminal surface of the wall and the elongate flexible element extending from the anchor member and out of the luminal surface of the body passage wall and with the abluminal surface of the body passage wall overlying the implanted anchoring device remaining unpunctured;
   wherein said wall of a body passage comprises a mucosa layer, a submucosa layer, a muscle layer, and an adventitia layer or a serosa layer; and
   wherein the mucosa layer defines said luminal surface and wherein the adventitia layer or serosa layer defines said abluminal surface.

2. The method of claim 1, wherein said applying suction comprises applying suction through a first working channel of an endoluminally advanceable device.

3. The method of claim 2, wherein said inserting includes forcing the anchor member of said anchoring device into said wall with a delivery device.

4. The method of claim 3, wherein said delivery device comprises a needle.

5. The method of claim 4, wherein said endoluminally advanceable device includes a second working channel, and wherein said needle is translatable through said second working channel.

6. The method of claim 2, wherein a distal segment of the endoluminally advanceable device has a longitudinal axis, and wherein the anchoring device is inserted into the pseudopolyp of tissue at an offset angle from said longitudinal axis.

7. The method of claim 1, wherein said applying suction step occurs prior to said implanting the anchor member step.

8. The method of claim 1, wherein said applying suction step causes the creation of the pseudopolyp of tissue and causes penetration of the delivery instrument into said pseudopolyp of tissue.

9. The method of claim 1, wherein during said implanting said delivery instrument does not extend past the distal opening of said tissue receiving chamber.

10. The method of claim 1, wherein said anchoring device is a T-anchor.

11. The method of claim 1, wherein said implanted anchoring device includes an elongate element extending into a lumen of the body passage wall, wherein the body passage wall comprises an alimentary canal.

12. The method of claim 11, wherein said elongate element comprises suture material.

13. The method of claim 12, further comprising:
   displacing the body passage wall during said inserting.

14. The method of claim 11, wherein the alimentary canal comprises an alimentary canal wall which includes stomach tissue.

15. A method of delivering an anchoring device into a wall of a body passage, the method comprising:
   providing an anchoring device;
   providing an endoluminally advanceable device including a tissue receiving chamber having a distal opening;
   receiving a volume of tissue of said wall in the tissue receiving chamber, wherein said volume of tissue is constituted of tissue of a segment of the body passage wall aligned with said distal opening, and said volume of tissue is constituted of only a portion of a thickness of said segment of the wall of a body passage so as to leave an abluminal surface of said segment of the body passage wall positioned exterior of said tissue receiving chamber;
   implanting said anchoring device in the body passage wall which includes inserting said anchoring device into said volume of tissue by delivery from a delivery instrument inserted only partially through the body passage wall;
   leaving the anchoring device implanted in the body passage wall with the anchoring device having not exited an abluminal surface of the wall and with the abluminal surface of the body passage wall overlying the implanted anchoring device remaining unpunctured;
   wherein said wall of a body passage comprises a mucosa layer, a submucosa layer, a muscle layer, and an adventitia layer or a serosa layer;
   wherein the mucosa layer defines a luminal surface and wherein the adventitia layer or serosa layer defines said abluminal surface.

16. The method of claim 15, wherein said receiving includes drawing said volume of tissue into the tissue receiving chamber.

17. The method of claim 15, wherein said tissue receiving chamber has a longitudinal axis, and wherein said anchoring device is inserted into said volume of patient tissue at an offset angle from said longitudinal axis.

18. A method of delivering an anchoring device into a wall of a body passage, the wall having a luminal surface and an abluminal surface, the method comprising:
   providing an endoluminally advanceable device that includes a tissue receiving member defining a tissue receiving chamber, the tissue receiving member having a distal end defining a distal opening of the chamber;

providing an anchoring device positioned in the tissue receiving chamber, the anchoring device including an anchor member and a flexible elongate element attached to the anchor member;

positioning said distal end of said tissue receiving member against said luminal surface, and applying suction to the luminal surface of the body passage wall so that a portion of a thickness of the wall is sucked into the tissue receiving chamber and wherein said abluminal surface is positioned exterior of said tissue receiving chamber; and delivering the anchor member of said anchoring device into the wall through said luminal surface from a delivery instrument as said wall portion is being sucked into the tissue receiving chamber such that the anchor member is received completely within the wall with the elongate flexible element extending from the anchor member and out of the luminal surface of the wall and with the abluminal surface of the body passage wall overlying said anchoring device remaining unpunctured;

wherein said wall of a body passage comprises a mucosa layer, a submucosa layer, a muscle layer, and an adventitia layer or a serosa layer; and wherein the mucosa layer defines said luminal surface and wherein the adventitia layer or serosa layer defines said abluminal surface; and wherein during said delivering said delivery instrument does not extend distally past the distal end of said tissue receiving member.

19. The method of claim 18, wherein said anchoring device is left implanted in the wall without having exited the abluminal surface of the wall.

\* \* \* \* \*